US008048656B2

(12) United States Patent
de Bont et al.

(10) Patent No.: US 8,048,656 B2
(45) Date of Patent: Nov. 1, 2011

(54) PROCESS FOR THE PRODUCTION AND RECOVERY OF HYDROCARBONS

(75) Inventors: Jan de Bont, Wageningen (NL); Paulus Josephus Theodorus Bussmann, Apeldoorn (NL); Earl Lawrence Vincent Goetheer, Westdorpe (NL); Zhuo Hornstra-Xu, Amersfoort (NL); Dionne Josephine Irving, Apeldoorn (NL); Jan Izaak Walpot, Apeldoorn (NL); Johan Alexander Vente, Heteren (NL)

(73) Assignee: Nederlandse Organisatie voor toegepast-natuurwetenschappelijk Onderzoek TNO, VK Delft (NL)

( * ) Notice: Subject to any disclaimer, the term of this patent is extended or adjusted under 35 U.S.C. 154(b) by 0 days.

(21) Appl. No.: 10/590,860

(22) PCT Filed: Mar. 1, 2005

(86) PCT No.: PCT/NL2005/000147
§ 371 (c)(1),
(2), (4) Date: Apr. 23, 2007

(87) PCT Pub. No.: WO2005/083099
PCT Pub. Date: Sep. 9, 2005

(65) Prior Publication Data
US 2007/0275445 A1 Nov. 29, 2007

(30) Foreign Application Priority Data
Mar. 1, 2004 (EP) .................................. 04075638

(51) Int. Cl.
*C12P 7/22* (2006.01)
*C12P 7/42* (2006.01)
*C12P 7/40* (2006.01)

(52) U.S. Cl. ........ 435/156; 435/134; 435/135; 435/136; 435/146

(58) Field of Classification Search ........................ None
See application file for complete search history.

(56) References Cited

FOREIGN PATENT DOCUMENTS

| EP | 1 306 128 A1 | 5/2003 |
|---|---|---|
| WO | WO0018942 | 4/2000 |
| WO | WO0073485 | 12/2000 |
| WO | WO 2002/16030 A1 | 2/2002 |

OTHER PUBLICATIONS

Stark, David., In Situ Product Removal (ISPR) in Whole Cell Biotechnology During the Last Twenty Years, *Advances in Biochemical Engineering/Biotechnology* 2003, 80:149-175.
Kornmann, et al., Novel Type of in Situ Extraction: Use of Solvent Containing Microcapsules for the Bioconversion of 2-Phenylethanol From L-Phenylalanine by *Saccharomyces Cerevisiae, Biotechnology and Bioengineering* 2003, 83(4):376-385.
Einicke, et al. In-Situ Recovery of Ethanol from Fermentation Broth by Hydrophobic Adsorbents, *Acta Biotechnologica* 1991, 11(4):353-358.
Walpot, Jan. In-situ Product Recovery (ISPR) in Bioproductions, Meeting PI-network, Dec. 7, 2004.
Serp et al., Enhancement of 2-Phenylethanol Productivity by *Saccharomyces cerevisiae* in Two-Phase Fed-Batch Fermentations Using Solvent Immobilization, Biotechnology and Bioengineering, vol. 82, No. 1, Apr. 5, 2003, p. 103-110.
Zheng et al., A Model of Fixed Bed for Extracting Erythromycin with Porous Media Impregnated by Solvent, Chemical Industry and Engineering, 2001, vol. 18, No. 5, p. 300-302.
Yue et al., The Preparation of Solvent Impregnated Resins and Their Application to the Isolation of Spiramycin, Chinese J. Antibiotics, 1990, vol. 15, No. 2, p. 90-96.
Friesen et al., Recovery of Citric Acid from Fermentation Beer Using Supported-Liquid Membranes, Journal of Membrane Science, 1991, vol. 56, p. 127-141.
Patnaik, Liquid Emulsion Membranes: Principles, Problems and Application in Fermentation Processes, Biotechnology Advances, 1995, vol. 13, No. 2, p. 175-208.

*Primary Examiner* — Herbert J. Lilling
(74) *Attorney, Agent, or Firm* — Hoffmann & Baron, LLP

(57) ABSTRACT

The invention is directed to a process for the production and recovery of chemicals, in particular hydrocarbons, from a fermentation medium, wherein solvent impregnated carriers are used. Accordingly, the invention provides a process for the production of hydrocarbon from a fermentation liquid comprising: —forming said hydrocarbon from said fermentation liquid using a biocatalyst; —contacting said fermentation liquid with a solvent impregnated porous carrier, which solvent impregnated porous carrier has a density that is different from said fermentation liquid, whereby said formed hydrocarbon is sorbed by said solvent impregnated carrier; —regenerating said solvent impregnated carrier, whereby a stream of said hydrocarbon is obtained; and optionally, recycling said regenerated solvent impregnated carrier.

15 Claims, 1 Drawing Sheet

PROCESS FOR THE PRODUCTION AND RECOVERY OF HYDROCARBONS

This application is the U.S. National Phase of, and Applicant claims priority from, International Application Number PCT/NL2005/000147 filed 1 Mar. 2005, and European Patent Application bearing Ser. No. EP 04075638.9 filed 1 Mar. 2004, all of which are incorporated herein by reference.

BACKGROUND OF THE INVENTION

The invention is directed to a process for the production and recovery of chemicals, in particular hydrocarbons, from a fermentation medium.

Production of hydrocarbon starting materials by fermentation is an alternative to production from petroleum. Fermentation uses renewable resources and creates much less hazardous waste. The fermentative production of a few chemicals has been reported. Unfortunately, this is not a commercially feasible alternative for a great many desirable compounds because the compound of interest is produced in small amounts by the biocatalytic organisms. Even organisms that are genetically engineered to produce enhanced amounts of the desired compound often do not produce concentrations of the product high enough to justify the investments necessary to develop a commercial biofermentation process. This can be particularly true when the product is toxic to the cells or is regulated by a negative feedback mechanism, thereby limiting the potential concentration of the product in the fermentation medium.

WO-A-00/18942 describes a process wherein 4-hydroxybenzoic acid (PHB) is produced by fermentation. According to this process, the product PHB is removed from the fermentation during at least a portion of the fermentation by passing the fermentation medium through an anion exchange resin which binds PHB. Subsequently the anion exchange resin is extracted to remove bound PHB. Although this known process is said to result in improvements in recovery of the product and higher production of the product by the biocatalyst, there remain a number of disadvantages. First, the ion exchange resin needs to be applied in the form of a packed bed, which may result in considerable pressure drop and fouling of the bed. Moreover, ion exchange resins may have a negative influence on the biocatalyst (i.e., the microorganisms), since these resins can be poisonous to these biocatalysts. It is also possible that these resins bind essential nutrients for the biocatalyst. Also ion exchange resin particles are susceptible to biofouling. For these and other reasons, the extraction of product from the medium is carried out by contacting the medium in-stream (viz. outside the fermentor) with the resin, so that contact between resin and biocatalyst is minimized. Furthermore, because of fouling (viz. attachment of biocatalyst to the resin surface, resulting in decreased sorption capacity of the resin) of the resin, amongst others, it is not possible to carry out this process in a continuous fashion. For these reasons, the product yield of the process of WO-A-00/18942, like the product yield of other known processes, is limited.

Furthermore, WO-A-00/73485 describes a process for the extraction of a fermentation product from a broth, using a solvent that is encapsulated in a membrane. However, this process, as well as other membrane based processes for the recovery of products from fermentation processes, are hampered by slow absorption kinetics, as a result of the mass transfer barrier posed by the membrane. In addition, regeneration of these capsule absorbentia is generally difficult. Furthermore, the preparation of the encapsulated solvent is cumbersome.

Alternatively, liquid-liquid extraction by directly contacting the broth with a solvent for the product generally is also not an option, since this generally does not result in the desired suspended droplets of solvents which subsequently coalesce so that they could be separated by gravity, but rather this leads to the formation of an emulsion. These emulsions may be very stable and consequently it is very difficult or impossible to obtain the product from the solvent.

It is an object of the present invention to provide a process for the production of hydrocarbons, such as 4-hydroxybenzoic acid and benzaldehyde, which process, at least in part, overcomes the above-mentioned disadvantages. Other examples of hydrocarbons that may be produced according to the present invention are catechols (e.g. 3-methylcatechol), benzylalcohol, cinnamic acid, as well as mixtures of these and other hydrocarbons. In general, each compound (of commercial value) that can be extracted using a suitable solvent.

It has been found that by using solvent impregnated porous carrier particles, which particles may either float or sink in the broth, to perform the separation of the product from the broth in the fermentation process, this object can be met.

SUMMARY OF THE INVENTION

Thus, in one aspect the present invention is directed to a process for the production of hydrocarbon from a fermentation liquid comprising the steps of:
  forming said hydrocarbon from said fermentation liquid using a biocatalyst;
  contacting said fermentation liquid with a solvent impregnated porous carrier, whereby said formed hydrocarbon is sorbed by said solvent impregnated carrier;
  regenerating said solvent impregnated carrier, whereby a stream comprising said hydrocarbon is obtained; and
  optionally, recycling said regenerated solvent impregnated carrier.

By recycling is meant feeding at least part of said regenerated solvent impregnated carrier to the step of contacting said fermentation liquid with the porous solvent impregnated carrier.

The term "sorption" as used herein, covers absorption, adsorption and extraction or dissolution in solvent as well as combinations thereof. This term is also intended to cover absorption or adsorption as a result of chemical reaction of the product component in the solvent, which may be assisted by including additives in the solvent, so as to facilitate reactive extraction.

Serp et al. (Biotechnology and Bioengineering, 82(2003) 103-110) describe the use of a composite resin comprising an organic solvent (dibutylsebacate) entrapped in a polymeric matrix of polyethylene for the enhancement of 2-phenylethanol productivity in an experimental set up. The fermentation broth is contacted with the composite resin by passing the broth over a fixed bed of the resin particles. Porous impregnated carriers are not disclosed in this document.

Cao et al. (Huaxue Gongye Yu Gongcheng/Chemical Industry and Engineering 18(2001)300-302 describes extraction using porous media impregnated by solvent in a fixed bed.

Guan et al. (Kangshengshu 15(1990)90-96) describe the preparation of solvent impregnated resins. Also here only a filed bed set-up is disclosed.

A very important advantage that is obtained by employing the porous particles in accordance with the present invention is that their flotation behavior can be controlled, as will be set out in more detail hereinbelow. This allows for an effective means for separating the particles from the fermentation broth and thus for a process that can easily be adopted to an industrial scale.

DETAILED DESCRIPTION OF THE INVENTION

Figure 1:
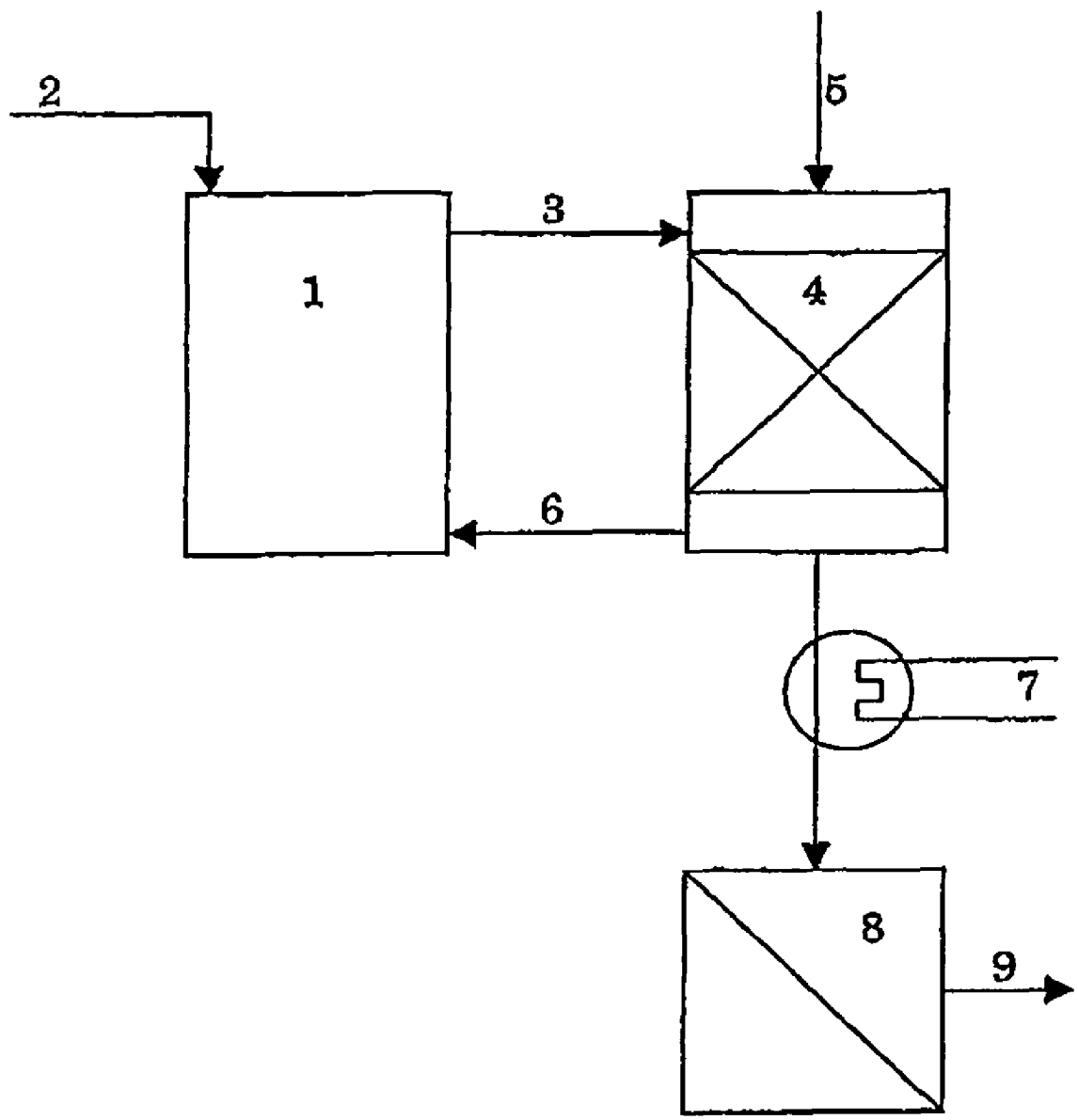
FIG. 1 is a schematic depicting a suitable configuration for carrying out the present invention.

In accordance with the present invention the solvent impregnated porous carrier has a density that is different from the density of the fermentation liquid. In practice this means that the carrier particles either rise in the liquid and float thereon, so that they may be collected easily from the top section of the fermentor, or that the carrier particles sink and accumulate in the bottom section of the fermentor and may be collected easily from the bottom section. The flotation or sedimentation behavior of the carrier particles can be engineered by choosing the appropriate porous solid material, that is, with the appropriate apparent density (which is a result of the porosity and the density of the solid material), and appropriate choice of the solvent (density). Furthermore, the density of the medium influences the rising or sedimentation velocity of the carrier particles, in particular the gas hold-up. In addition the diameter of the porous impregnated carrier is of influence to the flotation or sedimentation behaviour.

The flotation or sedimentation behaviour may be further influenced during operation of the process of the present invention by agitating the fermentor vessel, e.g. by using a stirring device.

The solvent impregnated carrier (by the present inventors sometimes also referred to as "SISCA", which is an acronym for "solvent impregnated smart carrier") that is used according to the present invention comprises a porous carrier and a solvent immobilized in the pores of said porous carrier. The carriers are suitably in the form of small particles typically having a diameter of several tenths of mm to several mm, e.g. 0.3 mm to 20 mm, preferably 0.4 mm to 5 mm. It was found that for these dimensions an optimal balance is obtained between mass transfer properties on the one hand and ease of separation of the SISCA containing the product from the fermentation broth on the other hand. The carriers can be made of any material that is non-biodegradable and has a binding with the solvent that is sufficiently strong to immobilize the solvent. The carrier material is hydrophobic. It must furthermore be able to withstand the regeneration conditions, e.g. steam of high temperature, when regeneration is carried out with steam. Also, to avoid infection of the fermentor with foreign microorganisms, the carrier material must be such that it can be sterilised without degrading.

The porosity of the solvent impregnated carrier is preferably chosen such that the particles have average pore diameter of from 25 Å (2.5 nm) to 50 µm, more preferably from 0.02 µm to 25 µm. WO-A-02/16030 describes processes to obtain solvent impregnated carrier particles having these suitable pore diameters.

The porosity of the solvent impregnated carrier is preferably from 30-80 vol. %. Higher porosities than 80 vol. % generally improve the absorption capacity of the particles, but this may entail a decrease in the mechanical stability of the particles. At porosity values lower than 30 vol. % the absorption capacity may become too low for certain applications. More preferably the porosity ranges from 40-60%, e.g. about 50%.

Preferably the carrier comprises a polymeric material, although certain types of ceramic material such a silica, zirconium oxide, alumina or aluminosilicates (e.g. zeolites) may be used as well. Preferably the carrier comprises a crosslinked polymeric material, e.g. polymers crosslinked with divinylbenzene (DVB). Preferred polymers are polystyrene, polyethylene, polyvinylchloride and polypropylene, optionally crosslinked. Other suitable polymeric materials are polymeric resins such as Amberlite™ resins, e.g. XAD4 or XAD16, which are based on a hydrophobic polymer of styrene and DVB. Typically, the carrier is obtained by extrusion of the (polymeric) material.

The pores in the carrier particles have dimensions that preferably range from 0.01 to 50 µm, more preferably from 0.02 µm to 25 µm, e.g. from 0.03 to 20 µm. The porosity of the carrier particles is preferably from 30-80 vol. %, e.g. from ca. 65 to ca. 80 vol. %, such as from 70 to 75 vol. %.

Suitable solvents for use in the present invention are those that display sufficient bonding with the carrier, viz. the solvent must have a suitable surface tension. Furthermore, the solvent should have a sufficient affinity for the hydrocarbon to be recovered from the medium, viz. the distribution coefficient should be favourable. The solvent should have a low water solubility to avoid losses of solvent when in contact with the fermentation medium. The solvent should not be too volatile, so as to avoid evaporation as much as possible. It should not be explosive. Also it should essentially not be biodegradable under the conditions employed. The solvent must be able to withstand the regeneration step. Moreover, it should preferably be possible to sterilize the solvent if this is required.

Suitable solvents are in general non-aqueous solvents that are non-miscible with water. Suitable solvents include di-isodecylphtalate (DIIP), castor oil, octanol, decanol, cumene, petroleum ether, hexane, octane, benzene, palm kernel oil, soy oil, and mixtures thereof. Typically the solvent is applied in a weight ratio of porous carrier adsorbent to solvent in the range of 0.1 to 2, e.g. from 0.2 to 1. Complexing agents may be added to the solvents to facilitate the absorption of fermentation products.

Suitable microorganisms (biocatalysts) for use in the present invention are in general bacteria, yeasts and moulds. More specifically, one or more of *Pseudomonas putida, Escherichia coli, Sacharomyces cerevisiae, Lactobacillus* species, *Aspergillus niger*, and the like can be used. It is also possible to use only the biochemically relevant components of the above-mentioned microorganisms, such as certain enzymes.

One of the advantages of the present invention is that it provides integration of production by biochemical reaction and separation. Thus these processes may be combined in a simple unit operation, which reduces installation and operating costs considerably. In this way, in situ sorption of the products takes place, which ensures favourable reaction conditions, since product inhibition of the biocatalyst no longer occurs or occurs to a more limited extent.

The solvent impregnated carriers used in the present invention may be prepared by methods known in the art. For instance, polymers may be impregnated with the solvent by simply contacting the carrier polymer with a mixture of the solvent and a second, more volatile solvent. After impregnation, the more volatile solvent is evaporated under reduced pressure and/or increased temperature, by which the solvent impregnated carrier is obtained. It is also possible to melt a polymer carrier at a high temperature and subsequently mix the molten polymer with the solvent and optional carriers. During cooling, a porous polymeric matrix is formed, the pores of which are filled with the solvent, thus forming the solvent impregnated particles.

According to the present invention the hydrocarbon when it is formed is absorbed and/or adsorbed from the broth by the solvent impregnated carrier, thus in effect extracted by the porous solvent impregnated carrier from the broth. This means that the hydrocarbon can be dissolved in the solvent, which is carried by the solvent impregnated material, it may adsorb on the surface of the carrier particles, or both. In addition to dissolving in the solvent, it is also possible that the hydrocarbon undergoes a chemical reaction in or with the solvent, by which sorption of the hydrocarbon from the medium is improved. In order to improve chemical reaction, certain agents may be present in the solvent. These agents should be mechanically and biologically stable, must have a strong but reversible interaction with the hydrocarbon, must be selective for the hydrocarbon to be produced as compared to other components, must be essentially insoluble in water and soluble in the extraction solvent, must provide for sufficiently fast reaction kinetics, and must be able to withstand the regeneration conditions. In general the same requirements given for the solvent hereinabove apply to these agents. Examples of such agents are complexing agents, such as amines, e.g. tri-octylamine, di-ethylamine, tri-ethylamine; or certain organo-phosphorus compounds such as DEHPA (di-(2-ethylhexyl)phosphoric acid), DEHTPA (di(2-ethylhexyl) dithiophosphoric acid), HEHEHP (2-ethylhexyl-phosphonic acid mono-2-ethylhexyl ester).

The contacting of the fermentation liquid with the solvent impregnated carrier can be effected in any known manner. In one embodiment, a configuration is used wherein the particles are fed at the bottom of the fermentor and are allowed to rise due to the density difference of the particles and the fermentation liquid. Thus, the density of the solvent impregnated particles (solvent+carrier) in this embodiment, is preferably less than the density of water. More preferably the density of the solvent impregnated particles is about 900 kg/m$^3$ or less.

Conversely, it is also possible to use particles that are heavier than the fermentation liquid, which particles are fed at the top of the fermentor and are allowed to sink to the bottom thereof.

The regeneration of the solvent impregnated carrier may be carried out by using steam (stripping), by back-extraction, by heating, or by combinations thereof. In one embodiment the regeneration is carried out using steam, by contacting the loaded carrier with e.g. steam having a temperature of 100 to 200° C. and a pressure of 1 to 20 bara.

Back-extraction involves contacting the loaded solvent impregnated carrier with a further solvent that has a higher affinity for the product than the solvent. If the product is chemically bonded by the additives present in the solvent or carrier, it can also be recovered by allowing the reverse reaction to the place, by which the product is released. For example, in the case of the back extraction of organic acids, alkaline solutions can be used.

FIG. 1 schematically shows a suitable configuration for carrying out the present invention. According to the embodiment depicted in FIG. 1, to fermentor (1) starting material (2) is fed, e.g. continuously. The starting material is converted to the hydrocarbon by the microorganisms in the fermentor. The fermentor can e.g. be a CSTR or a fluidized bed type reactor. It is also possible to operate the process intermittently, e.g. as a fed-batch. The solvent impregnated particles are fed to the fermentor at (6). In the fermentor (1) the solvent impregnated carriers, which are selective for the product hydrocarbon, become loaded with the product hydrocarbon. Subsequently the loaded carriers are recovered, preferably at the top of the fermentor. The carriers loaded with the product hydrocarbon (3) are then fed to a regeneration section. This may be in the form of a steam stripper (4), in which steam (5) is contacted with the loaded carriers. Operating conditions of the stripping section include a steam pressure of up to 20 bara. During stripping, the hydrocarbon evaporates from the solvent in the solvent impregnated carriers. The solvent itself remains in the carriers. A gaseous product stream leaves the stripping section, which after cooling at (7) is separated at (8) in an aqueous fraction (not shown) and the product stream (9). In the embodiment of FIG. 1, the solvent impregnated carriers are fed at (or near) the bottom of the fermentor. By selecting solvent impregnated carriers having a density that is lower than that of the broth in the fermentor (viz. a density typically lower than that of water), the carriers are allowed to travel upward and to become loaded with product. At (or near) the top of the fermentor the carriers can be collected very easily by simply skimming the carriers off.

Another option is to use solvent impregnated carriers with a higher density than the density of water. In that case the unloaded carriers are fed at or near the top of the fermentor and the loaded carriers are recovered at the bottom of the fermentor.

EXAMPLE

Porous cylindrical particles having a length of 1000 μm, a width of 800 μm, a pore diameter ranging from 0.1-10 μm, 50% porosity and a density of 520 kg/m$^3$ were impregnated with 1-octanol by contacting the particles with the octanol at room temperature during 30 minutes under stirring.

After impregnation, the particles had a density of 920 kg/m$^3$ and a low affinity for water.

The solvent impregnated porous carrier thus obtained was subsequently brought into a vessel in which a fermentation process was carried out (phenol producing *Pseudomonas putida*, which were previously adapted to octanol). The fermentation broth was vigorously mixed to keep the particles in suspension. The temperature was 30° C. After 18 hours the process was stopped and the particles were separated from the broth. The cell density (growth of micro organisms) was also determined. The concentration of phenol in the medium and in the particles was determined. The particles were subsequently regenerated using a solution of 2 M NaOH, which yielded pure phenol.

From these measurements it can be concluded that almost all of the phenol produced is extracted.

The invention claimed is:

1. A method for extracting a fermentation product from a fermentation liquid comprising:
   (i) conducting a fermentation using a biocatalyst to form a fermentation product in a fermentation liquid;
   (ii) contacting the fermentation liquid with a solvent-impregnated porous carrier, wherein the solvent-impregnated porous carrier has a density different from the fermentation liquid and the fermentation product is sorbed by the solvent-impregnated carrier; and
   (iii) separating the fermentation product from the solvent-impregnated porous carrier, wherein the fermentation product is phenol.

2. A method according to claim 1, wherein the separation is carried out by steam stripping, back-extraction, heating, or combinations thereof.

3. A method according to claim 1, wherein the solvent-impregnated porous carrier in step (iii) is recycled through to step (ii).

4. A method according to claim 1, wherein said solvent impregnated carrier comprises a polymeric carrier.

5. A method according to claim 4, wherein said polymeric carrier comprises one or more polystyrene, polypropylene, polytetrafluoroethylene, silicone, polyethylene, or regenerated cellulose group.

6. A method according to claim 5, wherein said polymeric carrier is crosslinked.

7. A method according to claim 1, wherein said solvent impregnated carrier comprises an inorganic carrier selected from silica, alumina, aluminosilicates, and combinations thereof.

8. A method according to claim 1, wherein said biocatalyst is selected from *Pseudomonas putida, Escherichia coli, Sacharomyces cerevisiae, Lactobacillus* species, or *Aspergillus niger*.

9. A method according to claim 1, wherein
said solvent impregnated carrier is inserted at or near the bottom of a fermentor containing said fermentation liquid and is collected at or near the top of said fermentor, wherein said solvent impregnated carrier has a density that is lower than that of said fermentation liquid; or
said solvent impregnated carrier is inserted at or near the top of a fermentor containing said fermentation liquid and is collected at or near the bottom of said fermentor, wherein said solvent impregnated carrier has a density that is higher than that of said fermentation liquid.

10. A method according to claim 1, which is carried out continuously.

11. A method according to claim 1, wherein said porous solvent impregnated carrier has an average pore diameter of from 2.5 nm to 50 μm.

12. A method according to claim 1, wherein the porosity is from 30 to 80%.

13. A method according to claim 1, wherein said biocatalyst is *Pseudomonas putida*.

14. A method according to claim 4, wherein said polymeric carrier comprises a polystyrene.

15. A method according to claim 1, wherein the separation is carried out by steam stripping.

* * * * *